(12) United States Patent
Yang et al.

(10) Patent No.: US 10,471,080 B2
(45) Date of Patent: Nov. 12, 2019

(54) USE OF TREHALOSE FOR PREVENTION OF NEURAL TUBE DEFECTS

(71) Applicants: Peixin Yang, Woodstock, MD (US); E. Albert Reece, Lutherville, MD (US)

(72) Inventors: Peixin Yang, Woodstock, MD (US); E. Albert Reece, Lutherville, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 13/901,784

(22) Filed: May 24, 2013

(65) Prior Publication Data

US 2013/0316971 A1    Nov. 28, 2013

Related U.S. Application Data (60) Provisional application No. 61/651,189, filed on May 24, 2012.

(51) Int. Cl.
*A61K 31/7016* (2006.01)
*A46B 15/00* (2006.01)

(52) U.S. Cl.
CPC ...... *A61K 31/7016* (2013.01); *A46B 15/0093* (2013.01); *A46B 2200/1046* (2013.01)

(58) Field of Classification Search
None
See application file for complete search history.

(56) References Cited

U.S. PATENT DOCUMENTS

2009/0017167 A1\* 1/2009 Krumhar et al. ............... 426/72
2009/0123580 A1\* 5/2009 Patel et al. ...................... 424/750

OTHER PUBLICATIONS

Allen, VM et al., Journal of Obstetrics and Gynaecology Canada, "Teratogenicity associated with pre-existing and gestational diabetes", 2007, vol. 29, No. 11, pp. 927-944.\*
Wentzel, P. et al., Diabetes, "Folic Acid Supplementation Diminishes Diabetes- and Glucose-Induced Dysmorphogenesis in Rat Embryos In Vivo and In Vitro", 2005, vol. 54, pp. 546-553.\*
Adastra et al.; A differential autophagic response to hyperglycemia in the developing murine embryo; *Reproduction*; vol. 141; pp. 607-615; 2011.
Chen et al.; Role of trehalose phosphate synthase and trehalose during hypoxia: from flies to mammals; *The Journal of Experimental Biology*; vol. 207; pp. 3125-3129; 2004.
Chen et al.; Superoxide is the major reactive oxygen species regulating autophagy; *Cell Death and Differentiation*; vol. 16; pp. 1040-1052; 2009.
Colell et al.; GAPDH and Autophagy Preserve Survival after Apoptotic Cytochrome c Release in the Absence of Caspase Activation; *Cell*; vol. 129; pp. 983-997; 2007.
Fimia et al.; Ambra1 regulates autophagy and development of the nervous system; *Nature*; vol. 447; pp. 1121-1125; 2007.
Mizushima et al.; Autophagy in mammalian development and differentiation; *Nature Cell Biology*; vol. 12; No. 9; pp. 823-830; 2010.
Mizushima et al.; In Vivo Analysis of Autophagy in Response to Nutrient Starvation Using Transgenic Mice Expressing a Fluorescent Autophagosome Marker; *Molecular Biology of the Cell*; vol. 15; pp. 1101-1111; 2004.
Salbaum et al.; Neural Tube Defect Genes and Maternal Diabetes during Pregnancy; *Birth Defects Research (Part A): Clinical and Molecular Teratology*; vol. 88; pp. 601-611; 2010.
Sarkar et al.; Trehalose, a Novel mTOR-independent Autophagy Enhancer, Accelerates the Clearance of Mutant Huntingtin and alpha-Synuclein; *The Jornal of Biological Chemistry*; vol. 282; No. 8; pp. 5641-5652; 2007.
Tanaka et al.; Trehalose alleviates polyglutamine-mediated pathology in a mouse model of Huntington disease; *Nature Medicine*; vol. 10; No. 2; pp. 148-154; 2004.

\* cited by examiner

*Primary Examiner* — Shaojia A Jiang
*Assistant Examiner* — Bahar Craigo
(74) *Attorney, Agent, or Firm* — Wenderoth, Lind & Ponack, L.L.P.

(57) ABSTRACT

Maternal diabetes suppresses autophagy in neuroepithelial cells of the developing neural tube which leads to neural tube defect formation. Trehalose treatment reversed autophagy impairment and prevented neural tube defects in diabetic pregnancies. Trehalose resolved homeostatic imbalance by correcting mitochondrial defects, dysfunctional proteins, ER stress, apoptosis, and delayed neurogenesis in the neural tubes exposed to hyperglycemia. Methods of using trehalose as an intervention against hyperglycemia-induced neural tube defects are provided herein.

10 Claims, 9 Drawing Sheets

USE OF TREHALOSE FOR PREVENTION OF NEURAL TUBE DEFECTS

STATEMENT OF FEDERALLY SPONSORED RESEARCH AND DEVELOPMENT

This invention was made with government support under Grant Numbers DK083243 and DK083770 awarded by the National Institutes of Health. The government has certain rights in the invention.

TECHNICAL FIELD

The invention relates to methods for reducing birth defects in developing embryos. More specifically, the invention relates to methods for preventing hyperglycemia-induced neural tube defects (NTDs) in embryos.

BACKGROUND OF INVENTION

Pregestational diabetes significantly increases the risk of NTDs, also known as diabetic embryopathy. There are 3-10 times more NTDs in offspring of diabetic mothers than those of nondiabetic mothers (3, 9, 32). Because optimal glycemic control is difficult to achieve and maintain, and even transient exposure to diabetes can cause NTDs, maternal diabetes-induced NTDs are significant health problems for both the mother and her child. The seriousness of these relationships is emphasized by the upsurge in diabetic pregnancies: nearly 3 million American women and 70 million women worldwide of reproductive age (18-44 years) have diabetes today, and this number is expected double by 2030. Although diabetes mellitus is a complex metabolic disease, hyperglycemia is the sole mediator of diabetes teratogenicity. Indeed, clinical studies have revealed a strong correlation between the degree of maternal hyperglycemia and the rate and severity of birth defects (14, 26). When whole rodent embryos are cultured in high concentrations of glucose, high glucose induces NTDs similar to those observed in human fetuses exposed to maternal diabetes (48).

An internationally-accepted rodent model of type 1 diabetes, which mimics the human condition seen in type 1 and type 2 maternal diabetes, can be used to study the pathogenesis of maternal diabetes-induced NTDs. Such studies (1, 13, 20, 21, 22, 30, 33) have revealed that cellular stress, including oxidative stress and endoplasmic reticulum (ER) stress, and enhanced neural progenitor apoptosis play central roles in the induction of NTDs by maternal diabetes. However, the molecular intermediates downstream of hyperglycemia remain elusive.

Autophagy, also referred as macroautophagy, is an intracellular process that degrades dysfunctional proteins and damaged cellular organelles, including ER and mitochondria. Autophagy is highly active in, and essential for, early embryonic development (39). The precise role of autophagy in early embryogenesis may be explained by its clearance of unnecessary cellular components, which, thus, facilitates remodeling during differentiation (27). Autophagy is initiated by the formation of a double-membrane structure, the autophagosome (12). At least fourteen genes are essential for autophagosome formation (27). Multiple lines of indirect evidence suggest that autophagy plays a role in diabetic embryopathy. First, diminished autophagy resulting from deletion of the autophagy/beclin-1 regulator 1 (Ambra1) gene induces neural progenitor apoptosis and NTDs (11) reminiscent of those observed in diabetic embryopathy. Second, both oxidative stress and ER stress, two central players in diabetic embryopathy, regulates autophagy (6). Third, autophagy can act as either a pro-survival or pro-apoptotic mediator under physiological and pathological conditions (19). Finally, dysfunctional proteins (43) and damaged cellular organelles, such as mitochondria (49) and ER (22), accumulate in cells of neurulation-stage embryos exposed to maternal diabetes.

Folate supplements are able to prevent about 70% of NTDs in humans (42) and reduce maternal diabetes-induced NTDs in animal models (45). However, recent studies suggest that high maternal folate supplementation during pregnancy may increase the risk of breast cancer (25) and inflammatory bowel diseases (35) in offspring. Studies have shown that inositol can prevent some of the folate-resistant NTDs (15). Like folate, inositol is an intracellular signaling molecule that regulates various cellular processes (46), and, thus, may adversely affect the offspring of diabetic mothers in the long term. Furthermore, inositol- and folate-resistant NTDs have been observed in mouse models (38).

In view of the predicted increase in diabetic embryopathy and the dearth of acceptable means for preventing the condition, the development of accessible, convenient, and effective prevention strategies against maternal diabetes-induced NTDs are urgently needed.

BRIEF SUMMARY OF INVENTION

After diligent efforts, and as reported herein, the inventors have developed effective means for preventing hyperglycemia-induced embryonic neural tube defects via the administration of the disaccharide trehalose to a pregnant subject or a subject intending to become pregnant, where the subject suffers from a disease or condition characterized by hyperglycemia, such as diabetes mellitus. Trehalose re-activates autophagy and restores cellular homeostasis by preventing cellular stress, mitochondrial defects, and delayed neurogenesis. The present invention thus establishes trehalose as an agent that can be used to prevent maternal diabetes-induced NTDs.

In a first embodiment, the present invention is drawn to methods for reducing the risk of a hyperglycemia-induced neural tube defect in an embryo, comprising administering a therapeutically-effective amount of trehalose to a pregnant subject or a subject intending to become pregnant, wherein the subject is hyperglycemic.

In a second embodiment, the present invention is drawn to methods for preventing a hyperglycemia-induced neural tube defect in an embryo, comprising administering a therapeutically-effective amount of trehalose to a pregnant subject or a subject intending to become pregnant, wherein the subject is hyperglycemic.

In a third embodiment, the present invention is drawn to methods for inducing autophagosome formation in embryonic neuroepithelial cells, comprising administering a therapeutically-effective amount of trehalose to a pregnant subject or a subject intending to become pregnant, wherein the subject is hyperglycemic.

In a fourth embodiment, the present invention is drawn to methods for inhibiting impairment of autophagosome formation in embryonic neuroepithelial cells, comprising administering a therapeutically-effective amount of trehalose to a pregnant subject or a subject intending to become pregnant, wherein the subject is hyperglycemic.

In a fifth embodiment, the present invention is drawn to methods for inducing autophagy in embryonic neuroepithelial cells, comprising administering a therapeutically-effective amount of trehalose to a pregnant subject or a subject intending to become pregnant, wherein the subject is hyperglycemic.

In a sixth embodiment, the present invention is drawn to methods for inhibiting autophagy impairment in embryonic neuroepithelial cells, comprising administering a therapeutically-effective amount of trehalose to a pregnant subject or a subject intending to become pregnant, wherein the subject is hyperglycemic.

In each of these embodiments, the hyperglycemia is diabetes mellitus-induced hyperglycemia, drug-induced hyperglycemia, or illness-induced hyperglycemia.

In each of these embodiments, the neural tube defect is failure of neural tube closure.

In each of these embodiments, the therapeutically-effective amount of trehalose is a formulation comprising between about 2% and about 10% trehalose in a volume of about 10 ml. Alternatively, the therapeutically-effective amount of trehalose is a formulation comprising at about 5% trehalose in a volume of about 10 ml.

In each of these embodiments, the therapeutically-effective amount of trehalose is an amount that achieves between about 200 and 500 ug/ml trehalose in the maternal blood. Alternatively, the therapeutically-effective amount of trehalose is an amount that achieves about 350 ug/ml trehalose in the maternal blood.

In each of these embodiments where the subject is pregnant, the therapeutically-effective amount of trehalose is administered to the subject daily for at least the first month of pregnancy.

In each of these embodiments where the subject intends to become pregnant, the therapeutically-effective amount of trehalose is administered to the subject daily from prior to conception through at least the first month of pregnancy.

In each of these embodiments, the therapeutically-effective amount of trehalose is administered to the subject orally or via parenteral administration.

In each of these embodiments, trehalose induces expression of one or more of ULK1, Beclin 1, Atg3, Atg5, and Ambra1.

In each of these embodiments, trehalose inhibits expression of one or more of p62 and Dap.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 1. Maternal diabetes suppresses autophagy in the developing neuroepithelium. (A) LC3-II levels in E8.75 embryos from nondiabetic (ND) and diabetic mellitus (DM) dams. n=3 (embryos from three dams per group). (B) LC3-II levels in cultured E8 embryos under control (100 mg/dl glucose) and high glucose (HG, 250 mg/dl) conditions with or without 25 μmol/L Chloroquine (Chlo). n=3 (three culture experiments). (C) Autophagosomes (blue arrow) including autophagolysosome (black arrow) in E8.75 neuroepithelial cells. Bar: 100 nm. Quantitative data was obtained by quantifying five images (image size: 9.43 μm$^2$) of each embryo. Three embryos (n=3) from three different mothers were used in per group. (D) Robust GFP-LC3 punctate foci were present in E8.75 embryonic neuroepithelial cells of the ND group. In contrast, diffused GFP-LC3 was expressed in neuroepithelial cells of the DM group. Bars=3.5 μM. (E) Quantitative GFP-LC3 punctate foci with a diameter greater than or equal to twenty pixels by Image J software in E8.75 neuroepithelial cells. (F) GFP-LC3 punctate foci in non-neuroepithelial cells adjacent to the neuroepithelium. n=3 (embryos from three dams per group).

FIG. 2. Trehalose prevents maternal diabetes-induced NTDs and autophagy impairment. (A) The trehalose treatment schematic. Trehalose was administrated in drinking water from E5.5. (B) NTD rates in nondiabetic (ND) and diabetic mellitus (DM) dams with or without 5% trehalose. NTD rates were calculated by litters. n=12 dams. (C) Numbers of normally developed embryos and NTD embryos. Chi$^2$ test was used in statistical analysis. (D) Morphology of E11.5 embryos and histological view of the neural tubes (NT). The blue lines indicate the levels of sections shown below. Bars=1 mm. (E) Total resorption rates calculated by group. (F) Blood glucose levels. (G) Serum and embryonic levels of trehalose in treated DM dams. n=12 dams. (H) LC3-II levels in E8.75 embryos. (I) Quantitative GFP-LC3 punctate foci in E8.75 neuroepithelial cells. (J) Number of autophagosomes. (K) Gene expression levels in E8.75 embryos. n=5 (embryos from five dams per group). * indicates significant difference comparing to other groups. In H, I and J, n=3 (embryos from three dams per group).

FIG. 4. Trehalose suppresses maternal diabetes-induced ER chaperone gene expression. mRNA levels of eIF2as1, calnexin, eIF2ak3, BiP, PDIA3, IRE1α, and CHOP in E8.75 embryos of the nondiabetic group (ND) and the diabetic mellitus group (DM), and the diabetic plus 5% trehalose group (DM-Tre). Four embryonic samples (n=4) from four different dams per group were used for RT-PCR. * indicates significant difference (P<0.05) compared to the other two groups in the same gene.

FIG. 5. Trehalose removes defective mitochondria and restores mitochondrial function resulting in blockade of apoptosis. Neuroepithelia from E8.75 embryos of nondiabetic (ND) and diabetic (DM) mice were analyzed. (A) Normal mitochondria having transversely oriented cristae enclosed by intact outer membranes. Defective mitochondria with disarrayed or disruptive cristae and decreased electronic density of the matrix (middle). Swollen mitochondria with entire loss of cristae (far right). (B) Defective mitochondria rates and total mitochondria. Defective mitochondria rate=number of defective mitochondria divided by total number of mitochondria. Levels of phosphorylated Bad (C), cleaved BID (D), cleaved caspase 3 and 8 (E) from the ND, the DM group, and the DM plus 5% trehalose group (DM-Tre). (F) Representative images of the TUNEL assays. Apoptotic cells were labeled in red, and all cell nuclei were labeled in blue. The dense V-shape blue areas marked by white dash lines were the anterior neuroepithelia. Bars were 30 μm. The red line in the E8.75 embryo picture at the far right indicates the level of the section shown in F. (G) Quantifications of apoptotic cell number. Apoptotic cells of the whole neuroepithelium including the dorsal and ventral domains. Five serial coronal sections though the anterior neural tubes of each embryo were analyzed. The numbers of apoptotic cells were counted in the neural tube area of each section and were averaged for each embryo. * indicates significant difference (P<0.05) compared to the other two groups.

FIG. 6. Trehalose significantly reduces maternal diabetes-induced dysfunctional proteins. Levels of protein modified by lipidperoxidation markers, 4-MDA (A) and 4-HNE (B), by nitrotyrosine (C), and by ubiquitin (D) were determined in E8.75 embryos from the nondiabetic group (ND), the diabetic mellitus group (DM), and the diabetic mellitus plus 5% trehalose group (DM-Tre) group. * indicates significant difference comparing to other groups. n =3 (embryos from three dams per group).

FIG. 7. Trehalose corrected maternal diabetes-delayed neurogenesis. (A, B, C, D) showed TuJ1 expressing (Green) terminally differentiated neurons in the developing neural tubes of nondiabetic (ND), diabetic mellitus (DM), and DM treated with trehalose (DM-Tre). Cell nuclei were stained by DAPI (Blue). Embryos from three dams per group were examined, and representative images were shown. Bars were 30 μm (A), 60 μm (B, C), and 150 μm (D).

FIG. 8. Trehalose corrected maternal diabetes-delayed neurogenesis. (A, B, C, D) showed Sox1 neural progenitors (Red) in the developing neural tubes of nondiabetic (ND), diabetic mellitus (DM), and DM treated with trehalose (DM-Tre). Cell nuclei were stained by DAPI (Blue). Embryos from three dams per group were examined, and representative images were shown. Bars were 30 μm (A), 60 μm (B, C), and 150 μm (D).

DETAILED DESCRIPTION OF THE INVENTION

I. Definitions

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

As reported herein, maternal diabetes diminishes autophagy in the developing neuroepithelium which leads to embryonic neural tube defects (NTDs). The present invention shows that trehalose re-activates autophagy and restores cellular homeostasis by preventing cellular stress, mitochondrial defects and delayed neurogenesis. The present invention also establishes trehalose as an agent that can be used to prevent maternal diabetes-induced NTDs.

As such, and in a first embodiment, the present invention is drawn to methods for reducing the risk of a hyperglycemia-induced neural tube defect in an embryo, comprising administering a therapeutically-effective amount of trehalose to a pregnant subject or a subject intending to become pregnant, wherein the subject is hyperglycemic.

In a second, related embodiment, the present invention is drawn to methods for preventing a hyperglycemia-induced neural tube defect in an embryo, comprising administering a therapeutically-effective amount of trehalose to a pregnant subject or a subject intending to become pregnant, wherein the subject is hyperglycemic.

In a third embodiment, the present invention is drawn to methods for inducing autophagosome formation in embryonic neuroepithelial cells, comprising administering a therapeutically-effective amount of trehalose to a pregnant subject or a subject intending to become pregnant, wherein the subject is hyperglycemic.

In a fourth embodiment, the present invention is drawn to methods for inhibiting impairment of autophagosome formation in embryonic neuroepithelial cells, comprising administering a therapeutically-effective amount of trehalose to a pregnant subject or a subject intending to become pregnant, wherein the subject is hyperglycemic.

In a fifth embodiment, the present invention is drawn to methods for inducing autophagy in embryonic neuroepithelial cells, comprising administering a therapeutically-effective amount of trehalose to a pregnant subject or a subject intending to become pregnant, wherein the subject is hyperglycemic.

In a sixth embodiment, the present invention is drawn to methods for inhibiting autophagy impairment in embryonic neuroepithelial cells, comprising administering a therapeutically-effective amount of trehalose to a pregnant subject or a subject intending to become pregnant, wherein the subject is hyperglycemic.

The trehalose used in the methods of the present invention is a naturally-occurring disaccharide formed by a 1,1-glucoside bond between two a-glucose units that is present in a wide variety of organisms, including plants, bacteria, yeast, and invertebrates.

Trehalose

Trehalose can be derived from corn starch and other sources (e.g., plant, bacterial, fungal, etc.). The main function of trehalose in these organisms is to protect cells against various environmental stresses (5).

The methods of the present invention are practiced on hyperglycemic subjects, i.e., those subjects exhibiting hyperglycemia. The hyperglycemia is diabetes mellitus-induced hyperglycemia, drug-induced hyperglycemia, or illness-induced hyperglycemia. Hyperglycemia, or high blood glucose level, is a condition in which an excessive amount of glucose circulates in the blood plasma. Hyperglycemia is generally defined as a blood glucose level above about 100 mg/dl (5.5 mmol/l). For example, the American Diabetes Association suggests a subject with a blood glucose level above 100 mg/dl is hyperglycemic (American Diabetes Association; see the website having the URL ending in diabetes.org).

Hyperglycemia is typically associated with and caused by diabetes mellitus; chronic hyperglycemia is a defining characteristic of the disease. Diabetes mellitus, or simply diabetes, is a group of metabolic diseases caused by low levels of insulin (type 1 diabetes mellitus) and/or resistance to insulin (type 2 diabetes mellitus). Diabetes mellitus also includes gestational diabetes where pregnant women without a previous diagnosis of diabetes develop a high blood glucose levels.

Hyperglycemia may also be caused by certain drugs, typically administered to a subject to treat a particular disease or condition, which induce high blood glucose levels. Such drugs include, but are not limited to, corticosteroids, octreotide, beta blockers, epinephrine, thiazide diuretics, niacin, pentamidine, protease inhibitors, L-asparaginase, some antipsychotic agents, acute uses of stimulants such as amphetamine, and psychotropic medications, such as olanzapine and duloxetine.

Hyperglycemia may further be caused by certain illness and medical conditions. For example, hyperglycemia may be found in subjects suffering from a stroke or myocardial infarction, and be associated with the following conditions: thyroid dysfunction, adrenal gland dysfunction, pituitary gland dysfunction, pancreatic disease, sepsis and other infections, intracranial diseases including encephalitis, brain tumors, brain bleeds, and meningitis, convulsive diseases, severe stress, and physical trauma.

In those methods of the present invention direct to reducing the risk of or preventing a neural tube defect in an embryo, the neural tube defect is a failure of neural tube closure.

The methods of the present invention are practiced by administering formulations comprising trehalose to a subject. Trehalose formulations may be administered to a subject via administration means that include, but are not limited to, oral, sublingual, intranasal, intraocular, rectal, transdermal, mucosal, pulmonary, topical and parenteral administration. Parenteral modes of administration include without limitation, intradermal, subcutaneous (s.c., s.q., sub-Q, Hypo), intramuscular (i.m.), intravenous (i.v.), intraperitoneal (i.p.), and intra-arterial. Any known device useful for parenteral injection or infusion of drug formulations can be used to effect such administration. In preferred aspects of each of the embodiments of the invention, trehalose formulations are administered to the subject orally.

Trehalose is formulated for administered to a subject in a formulation appropriate for the means of administration. For example, when the methods of the invention are practiced via oral administration, trehalose is formulated for oral administration. Exemplary oral formulations of trehalose include, but are not limited to, trehalose dissolved in water. Other acceptable oral formulations of trehalose that may be administered to a subject when the methods of the present invention are practiced include solid pills, liquid capsules, foods, and food supplements. Other exemplary means include, but are not limited to, trehalose formulated for parenteral administration.

The therapeutically-effective amount of trehalose administered to a subject will vary by factors including the weight of the subject, whether the subject is pregnant or intending to become pregnant, the gestational point at which treatment is begun, the means by which trehalose is administered, the physical nature of the trehalose formulation, and other relevant factors. While the clinician will be in the best position to prescribe the correct dosage, when a formulation is produced for oral administration in which trehalose is dissolved in water, therapeutically-effective amounts of trehalose-in-water formulations are defined by the volume of the formulation administered to the subject and the concentration of trehalose in the formulation.

Exemplary volumes of trehalose-in-water formulations to be administered to a subject that will have a therapeutic effect include, but are not limited to, about 5, 10, 15, 20, 25, 30, 35, 40, 45 or 50 ml. Exemplary volumes of trehalose-in-water formulations also include, but are not limited to, between about 1 and 500 ml, between about 1 and 250 ml, between about 1 and 100 ml, and between about 1 and 50 ml. As suggested above, the specific volume will vary based on the concentration of trehalose in the formulation, but an exemplary volume that is easily consumed by a subject is 10 ml.

Exemplary trehalose-in-water formulations include, but are not limited to, those comprising about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% trehalose, or more, in water. Exemplary trehalose-in-water formulations also include those comprising at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% trehalose, or more, in water. Exemplary trehalose-in-water formulations further include those comprising between about 0.1% and about 15%, between about 1% and about 10%, between about 2% and about 10%, between about 0.1% and about 5%, between about 1% and about 5%, between about 3% and about 8%, and between about 4% and about 6%, trehalose in water. In a specific aspect, the trehalose-in-water formulation comprises about 5% trehalose in water (0.5 g trehalose in 10 ml water). As suggested above, the specific concentration of trehalose in the formulation will vary based on the volume to be administered to the subject.

Alternatively, the therapeutically-effective amount of trehalose is an amount that achieves at least about 100, 120, 140, 160, 180, 200, 220, 240, 260, 280, 300, 320, 340, 350, 360, 380, 400, 420, 440, 480, 500, 520, 540, 560, 580, or 600 ug/ml, or more, trehalose in the maternal blood. The therapeutically-effective amount of trehalose may also achieves between about 100 and 1000 ug/ml trehalose in the maternal blood, or between about 100 and 750 ug/ml, between about 100 and 600 ug/ml, between about 200 and 500 ug/ml, or between about 200 and 400 ug/ml. In a specific aspect, the therapeutically-effective amount of trehalose achieves about 350 ug/ml trehalose in the maternal blood.

Administration frequencies of trehalose formulations will vary based on both the volume to be administered and the concentration of the formulation, among other factors, but acceptable frequencies include 4×, 3×, 2× or once daily, every other day, every third day, every fourth day, every fifth day, every sixth day, once weekly, every eight days, every nine days, every ten days, bi-weekly, monthly and bi-monthly. In preferred aspects, the trehalose formulations are administered twice a day (at 12 hours interval). The duration of treatment will be best determined by the attending physician. However, continuation of treatment is contemplated to last for at least the first month of a pregnancy, but may be extended to 5, 6, 7, 8, 9, 10 or more weeks into a pregnancy. For those subjects intending to become pregnant, treatment may begin within a few days before the date on which conception is first attempted and continued into the pregnancy for the periods noted above. Depending on the means of administration, the therapeutically-effective amount may be administered all at once, such as with an oral formulation in a capsule or liquid, or slowly over a period of time, such as with an intramuscular or intravenous administration.

In those methods of the present invention direct to reducing the risk of a neural tube defect in an embryo, the risk is reduced by about 99%, 98%, 97%, 96%, 95%, 94%, 93%, 92%, 91%, 90%, 89%, 88%, 87%, 86%, 85%, 84%, 83%, 82%, 81%, 80%, 75%, 70%, 65%, 60%, 55%, 50%, 45%, 40%, 35%, 30%, 25%, 20%, 15%, or 10%, or less, in comparison to a subject that has not been administered trehalose.

In methods of the invention directed to inducing autophagosome formation in embryonic neuroepithelial cells, autophagosome formation is induced by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99% or even 100% in comparison to autophagosome formation in embryonic neuroepithelial cells in a subject to which trehalose is not administered.

In methods of the invention directed to inhibiting impairment of autophagosome formation in embryonic neuroepithelial cells, impairment of autophagosome formation is inhibited by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99% or even 100% in comparison to autophagosome formation in embryonic neuroepithelial cells in a subject to which trehalose is not administered.

In methods of the invention directed to inducing autophagy in embryonic neuroepithelial cells, autophagy is induced by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99% or even 100% in comparison to autophagy in embryonic neuroepithelial cells in a subject to which trehalose is not administered.

In methods of the invention directed to inhibiting autophagy impairment in embryonic neuroepithelial cells, autophagy impairment is inhibited by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99% or even 100% in comparison to autophagy impairment in embryonic neuroepithelial cells in a subject to which trehalose is not administered.

In methods of the invention where trehalose induces expression of one or more of ULK1, Beclin 1, Atg3, Atg5, and Ambra1, expression of the genes is individually increased by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99% or even 100% in comparison to expression of the same gene in a subject to which trehalose is not administered.

In methods of the invention where trehalose inhibits expression of one or more of p62 and Dap, expression of the genes is individually decreased by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99% or even 100% in comparison to expression of the same gene in a subject to which trehalose is not administered.

The subjects upon which the methods of the present invention may be practiced include a human, non-human primate, bird, horse, cow, goat, sheep, a companion animal, such as a dog, cat or rodent, or other mammal. The skilled artisan will understand that in each instance the subject will be a female member of the species.

III. Examples

Materials and Methods

Mice. All animal procedures were approved by the University of Maryland School of Medicine Institutional Animal Care and Use Committee. Wild-type (WT) C57BL/6J mice were purchased from the Jackson Laboratory. The GFP-LC3 strain on a C57BL/6J background was originally created by Dr. Noboru Mizushima (28).

In vivo mouse model of diabetic embryopathy and morphologic assessment of NTDs. The mouse model of diabetic embryopathy was previously described (21, 22). Briefly, female mice were intravenously (i.v.) injected daily with 75 mg/kg streptozotocin (STZ) over two days to induce diabetes. Nondiabetic WT with vehicle injection served as controls. Diabetes was defined as 12-hour fasting blood glucose levels ≥250 mg/dl, which normally occurred at 3-5 days after STZ injections. There is no residual toxic effect caused by STZ in this animal model. Embryos were gathered at E8.75 (2:00 PM at E8.5) for analysis and at E11.5 from NTD examination.

Trehalose treatment and trehalose measurement. Concentrations of either 2% or 5% (gram/volume [ml]) trehalose (Cat#: T9531, Sigma) were given to WT nondiabetic and diabetic pregnant mice at E5.5 in drinking water. Trehalose levels in maternal serum and embryos were determined by the Trehalose Kit from Megazyme (Wicklow, Ireland).

Electron microscopy. The structures of autophagosome and mitochondria were examined by transmission electron microscopy (EM) in the University of Maryland EM core facility. Thick sections (1 μm) were cut and visualized at ×100 magnifications to identify the neuroepithelia of E8.75 embryos. Thin sections (80 nm) of identified neuroepithelia were cut and viewed with an electron microscope (Joel JEM-1200EX; Tokyo, Japan) under high-power resolution (10, 12 and 25 K) for identification of cellular organelle structures.

GFP-LC3 puncta analysis. GFP-LC3 transgenic (Tg) mice were used to quantify autophagy in vivo. E8.75 embryos were gathered, fixed in 4% paraformaldehyde (PFA) in PBS for 30 min at 4° C., quickly frozen, and cryosectioned at 5 GFP florescent images in embryonic neuroepithelial cells were recorded by confocal microscopy using a laser scanning microscope (LSM 510 META, ZEISS). GFP-LC3 punctate foci with a diameter greater than or equal to 20 pixels in each cell were calculated by Image J software according to the manufacturer's manual.

Immunofluorescent staining. E8.75 embryos were fixed in the methanol-chloroform-glacial acetic acid solution (6:3:1), embedded in paraffin and sectioned in 5 μM through the anterior neural tube. Deparaffinized sections were incubated with TuJ 1 antibody (Covance, #MMS-435P) at 1:400 dilution or Sox1 antibody (Cell Signaling, #4194) at 1:100 dilution in PBS with 10% heat-inactivated donkey serum overnight at 4° C. After washes in PBS, sections were incubated with secondary antibodies, Alexa Fluor® 488 Donkey Anti-Mouse IgG to TuJ1, and Alexa Fluor® 594 Donkey Anti-Rabbit IgG to Sox1. Cell nuclei were stained with DAPI (Blue). Immunofluorescent staining was examined by immunofluorescence microscopy. In order to visualize neurogenesis throughout the anterior neural tube, serial sections through the entire anterior neural tube were analyzed and representative images were shown. The earliest neurogenesis site was found at the boundary of midbrain and hindbrain. Five embryos from five dams per group were analyzed.

TUNEL assay. TUNEL assay was performed as previously described (21, 22). Briefly, 5-μm serial coronal sections through the forebrain-midbrain (FB-MB) boundary of the anterior neural tube were fixed with 4% PFA in PBS and incubated with TUNEL reaction agents. Closure at the FB-MB boundary is an essential step for closure of the anterior neural tube, and failed closure in this area results in exencephaly (2, 8). TUNEL-positive cells were counted in the neural tube area of each section. Based on the counting of total cell nuclei, the sizes of the neural tube areas of each section were relatively constant. Thus, apoptotic cell numbers were expressed as total TUNEL-positive cells per neural tube area. TUNEL assays were performed without the observer knowing the experimental group of the embryo examined.

Statistical analyses. Statistical differences were determined by Student's t-test for two group comparisons and One way ANOVA for more than two groups comparisons using SigmaStat 3.5 software. In ANOVA analysis, Tukey-test was used to estimate the significance of the results. Significant difference between groups in NTD incidence was analyzed by Chi-square test.

Results

Figure 1:
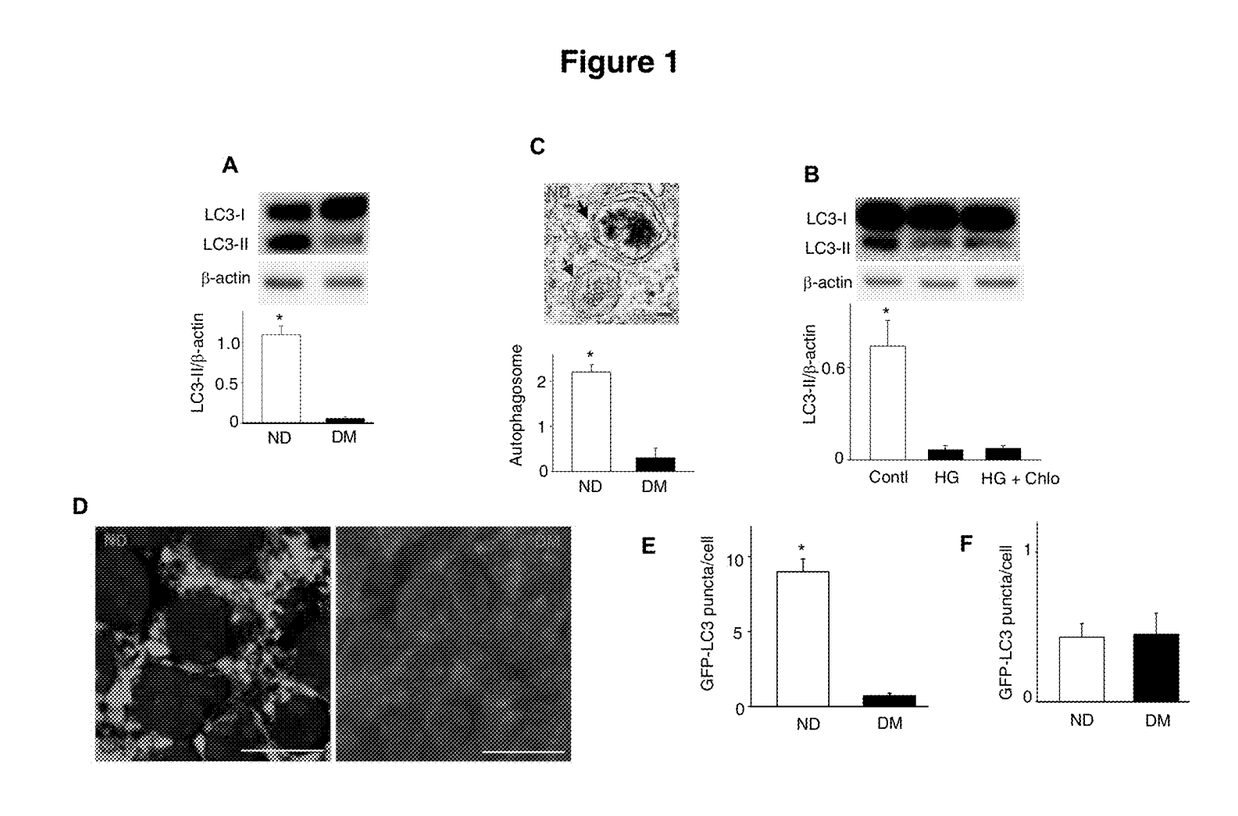

Maternal diabetes suppresses autophagy in neuroepithelial cells during embryonic neurulation. To determine whether maternal diabetes alters autophagy, levels of LC3-II (microtubule-associated protein 1 light chain 3), a reliable autophagy marker, were assessed in embryonic day 8.75 (E8.75) embryos. Maternal diabetes significantly decreased LC3-II levels (FIG. 1A). However, LC3-II reduction by maternal diabetes in vivo or high glucose in vitro was not due to increased lysosomal activity, because lysosomal inhibition by Chloroquine did not block high glucose-induced LC3-II reduction (FIG. 1B).

Whether autophagy impairment specifically occurs in neuroepithelial cells was then examined by subjecting sections from the E8.75 developing neural tube (neuroepithelium) to electron microscopy (EM). Consistent with the prior finding that autophagy is essential for neurulation (11), the EM study revealed that abundant autophagosomes were present in embryonic neuroepithelial cells under nondiabetic conditions (FIG. 1C). In contrast, the number of autophagosomes in embryonic neuroepithelial cells exposed to diabetes was significantly lower than that in neuroepithelial cells under nondiabetic conditions (FIG. 1C).

To confirm these EM findings, the GFP-LC3 transgenic mouse (GFP-LC3 Tg) was employed to quantify GFP-LC3 punctate foci, which is the most reliable in vivo method for determining autophagy activity (28). Robust autophagic GFP-LC3 puncta were observed in embryonic neuroepithelial cells under nondiabetic conditions (FIG. 1D). In contrast GFP-LC3 displayed a diffused pattern of expression in neuroepithelial cells exposed to diabetes (FIG. 1D). Maternal diabetes reduced autophagic GFP-LC3 puncta in neuroepithelial cells to approximately one tenth the level observed in the nondiabetic group (FIGS. 1D, E). Autophagy induction only occurs in neuroepithelial cells during the period of neurulation. Indeed, compared to the neuroepithelial cells, non-neuroepithelial cells under nondiabetic conditions had negligible numbers of autophagic GFP-LC3 puncta, which were not altered by diabetes (FIG. 1F). Collectively, these findings support the hypothesis that maternal diabetes specifically induces autophagy impairment in the neuroepithelial cells.

Figure 2:
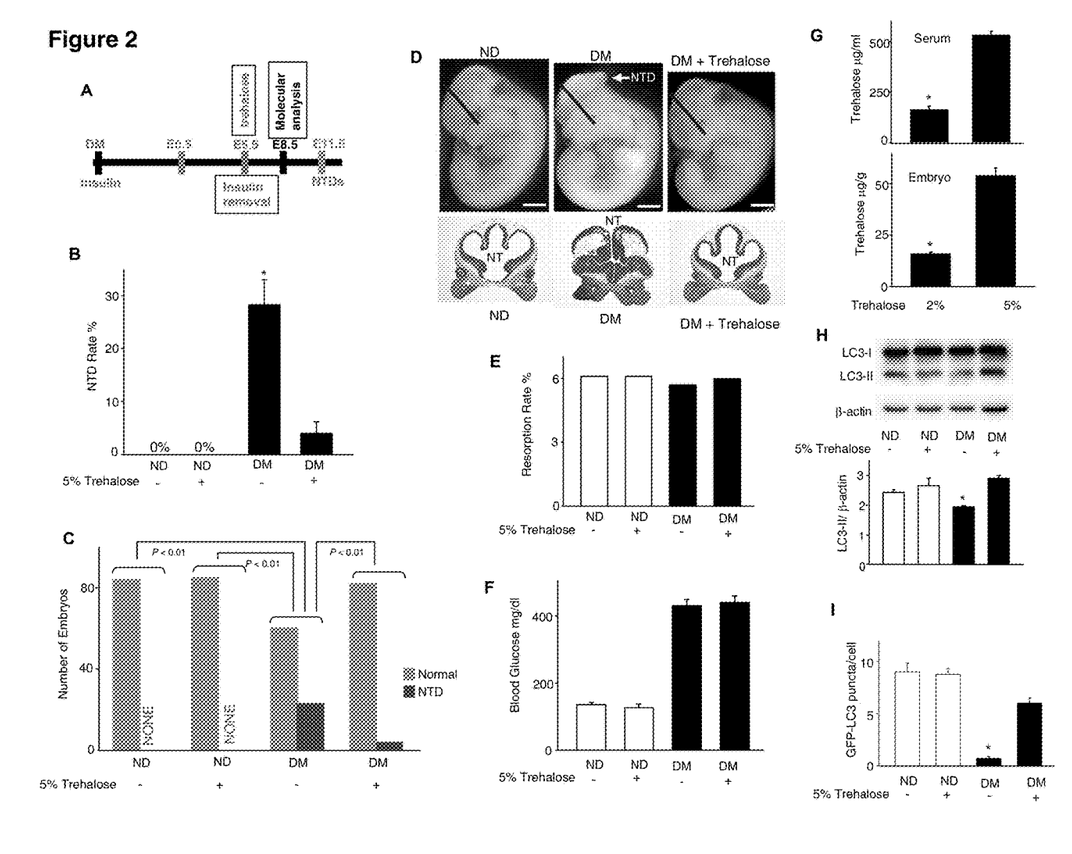

To determine whether altered gene expression leads to autophagy impairment in diabetes, all 17 known genes which regulate autophagy were surveyed. Maternal diabetes suppressed the expression of ULK1 (Atg1 in yeast), Atg 3, Atg5, Beclin 1 (Atg6), and Ambra1 (FIG. 2K), which are all essential for autophagosome formation. Maternal diabetes also simultaneously increased the expression of p62 (FIG. 2K), whose accumulation serves as an index of impaired autophagy (16), and Dap (FIG. 2K), which negatively regulates the autophagy processes. Thus, maternal diabetes induces autophagy impairment by altering gene expression that regulates autophagy.

Trehalose ameliorates maternal diabetes-induced NTDs by re-activating autophagy in neuroepithelial cells. Non-toxic reagents were sought to reverse autophagy impairment in diabetic embryopathy. Trehalose, a naturally occurring disaccharide, has been shown to possess autophagy stimulating activities in vitro (34). It was hypothesized that trehalose treatment would prevent maternal diabetes-induced NTDs by restoring autophagy activity. The NTD rate (4.0±2.2%) in embryos from diabetic dams treated with 5% trehalose water (weight/volume) was comparable to those in embryos from nondiabetic dams with or without trehalose treatment (0.0±0.0%) (FIGS. 2A, B, C, D), and was significantly lower than that in the diabetic group without trehalose treatment (28.3±4.7%) (FIGS. 2A, B, C, D).

Treatment with 2% trehalose also significantly reduced maternal diabetes-induced NTDs (Table 1) but to a lesser extent than did 5% trehalose treatment, demonstrating that trehalose reduces maternal diabetes-induced NTDs in a dose-dependent manner. Resorption rates did not differ between nondiabetic and diabetic dams with or without trehalose treatments (FIG. 2E), demonstrating that resorption is not a contributing factor in trehalose's ability to reduce NTDs. In agreement with one published report (37), trehalose treatment did not affect blood glucose levels in either nondiabetic or diabetic mice (FIG. 2F). Both 2% and 5% trehalose treatment resulted in 162.0±16.9 μg/ml and 503.9±19.3 μg/ml trehalose in maternal blood of diabetic dams, respectively (FIG. 2G), and embryonic trehalose levels were 15.8±1.0 μg/g tissue and 53.9±3.7 μg/g tissue in the 2% group and the 5% group, respectively (FIG. 2G). Thus, embryonic levels were proportionally related to maternal trehalose levels, demonstrating that maternal exposure to trehalose can effectively reach the developing embryo.

TABLE 1

Pregnancy outcomes at E11.5 in the nondiabetic and diabetic mice with or without 2% trehalose treatment

| Experimental Groups | Total Embryos | Total NTD Embryos | NTD Rate | Number of Dams | Resorption Rates |
|---|---|---|---|---|---|
| Nondiabetic | 70 | 0 | 0 | 11 | 4.2 |
| Nondiabetic + 2% trehalose | 29 | 0 | 0 | 4 | 4.8 |
| Diabetic | 83 | 23* | 27.7 | 12 | 4.6 |
| Diabetic + 2% trehalose | 41 | 4 | 9.8 | 5 | 4.7 |

*indicates significant difference (P < 0.05) when compared to other groups using $Chi^2$-test.
NTD rate = total NTD embryos/total embryos.

Trehalose treatment also restored maternal diabetes-diminished LC3-II expression (FIG. 2H). The number of autophagic GFP-LC3 puncta in neuroepithelial cells of the diabetic group treated with trehalose was restored to the level of that observed in the nondiabetic groups with or without trehalose treatment (FIG. 2I), and was significantly higher than that of the diabetic group without trehalose treatment (FIG. 2I). Because trehalose did not affect basal autophagy activities in neuroepithelial cells of the nondiabetic group (FIGS. 2H, I), subsequent analyses excluded the nondiabetic group treated with trehalose. Trehalose treatment blocked maternal diabetes-repressed autophagosome formation in neuroepithelial cells (FIG. 2J). Next, whether trehalose treatment corrects altered autophagy-related gene expression was determined. Trehalose treatment blocked the downregulation of ULK1, Beclin 1, Atg3, Atg5, and Ambra1, and the upregulation of p62 and Dap (FIG. 2K).

Figure 3:
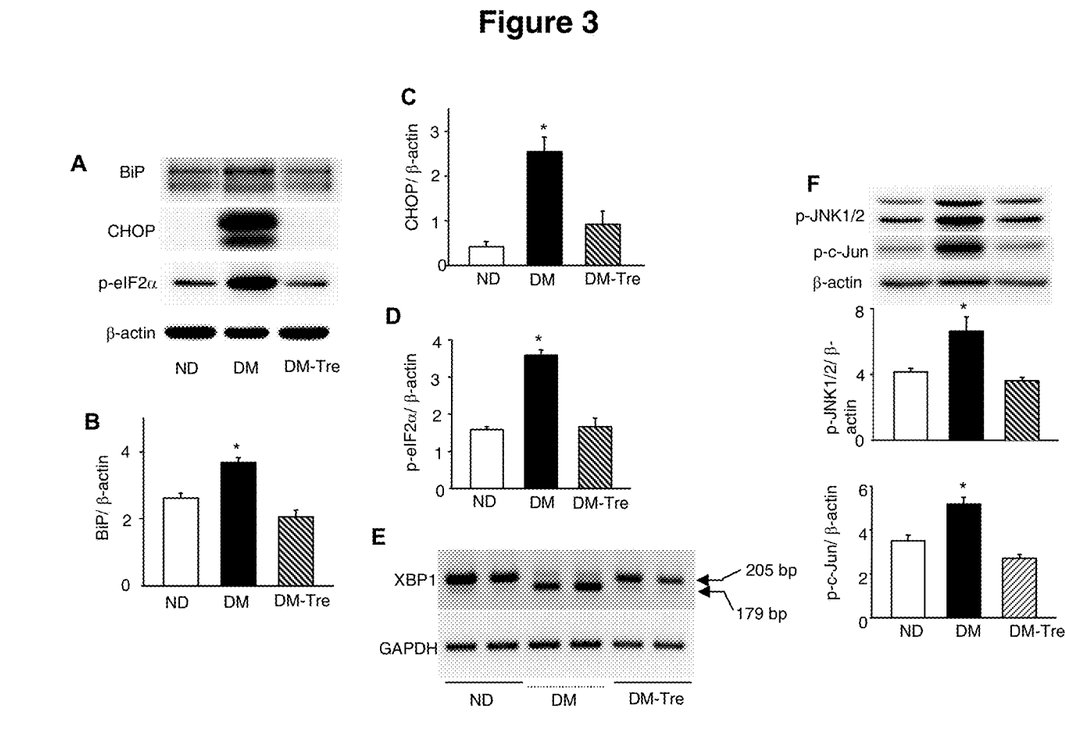
FIG. 3. Trehalose restored cellular homeostasis by blocking maternal diabetes-induced ER stress and JNK1/2 activation. The protein expression of ER markers, BiP (A, B), CHOP (A, C), and p-eIF2α (A, D), in E8.75 embryos of the nondiabetic (ND), the diabetic mellitus (DM), and the DM with 5% trehalose group (DM-Tre). (E) XBP1 splicing. (F) Levels of p-JNK1/2 and p-c-Jun. * indicates significant difference comparing to other groups. n=3 (embryos from three dams per group).
Figure 4:
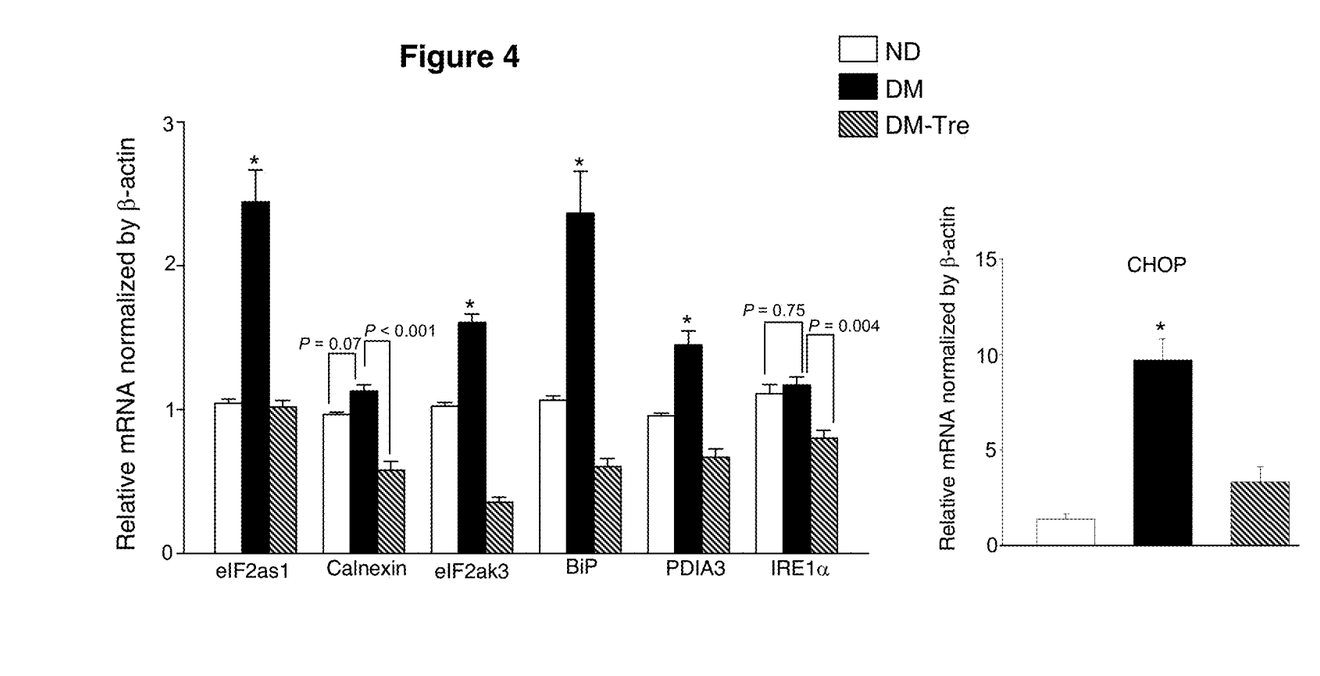

Trehalose blocks maternal diabetes-induced ER stress and its associated JNK1/2 activation. It had been previously demonstrated that ER stress and JNK1/2 activation are two interdependent causal events in maternal diabetes induced-NTD formation (22). It was therefore proposed that the autophagy activator, trehalose, could block ER stress and JNK1/2 activation in diabetic embryopathy. Consistent with the previous finding (22), maternal diabetes triggered ER stress (FIG. 3A-E), and trehalose treatment abrogated maternal diabetes-increased expression or phosphorylation of the ER chaperone proteins BiP (Binding immunoglobulin protein), CHOP (C/EBP-homologous protein), and Eukaryotic Initiation Factor 2α (eIF2 α) (FIGS. 3A, B, C, D). These ER chaperone proteins all serve as ER stress markers. In addition, maternal diabetes increased the expression of 7 ER chaperone genes, and this increase was abolished by trehalose treatment (FIG. 4).

Prolonged ER stress leads to X-box binding protein (XBP1) mRNA splicing (22), another reliable ER stress marker. Embryos under maternal diabetic conditions exhibited robust XBP1 splicing, which was manifested by a 179 bp band of the PCR products (FIG. 3E). On the other hand, trehalose treatment diminished XBP1 mRNA splicing (FIG. 3E). ER stress also is known to activate the pro-apoptotic c-Jun-N-terminal kinase 1/2 (JNK1/2) (40), which mediates the teratogenicity of diabetes (48). Trehalose completely abolished maternal diabetes-induced JNK1/2 activation (FIG. 3F) and its major downstream effector, c-Jun (FIG. 3F).

Figure 5:
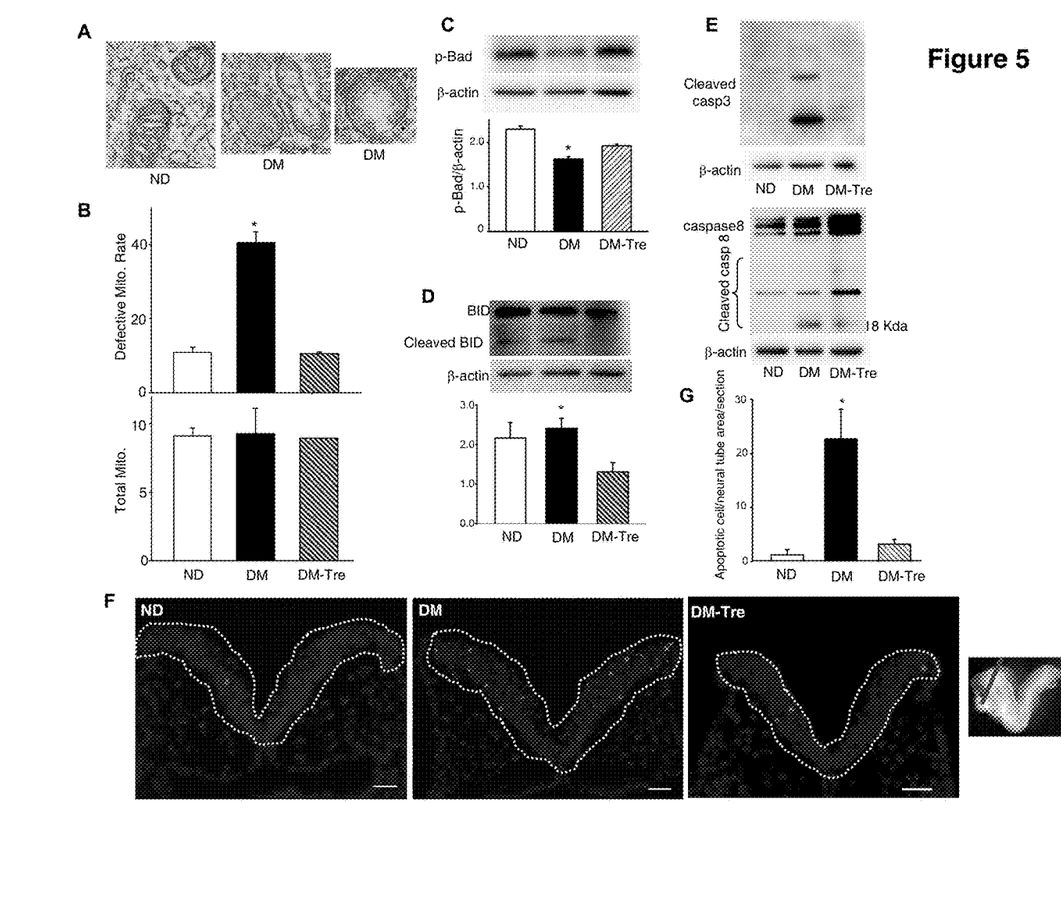

Trehalose removes defective mitochondria and oxidized proteins, thereby, protecting mitochondrial function and preventing neuroepithelial cell apoptosis. Mitochondrial dysfunction is associated with diabetic embryopathy (49). It was found that maternal diabetes significantly increased the number of defective mitochondria (FIGS. 5A, B); whereas it did not affect total number of mitochondria (FIG. 5B). Under diabetic conditions, trehalose treatment significantly reduced the number of defective mitochondria to a level comparable to that in the nondiabetic control group (FIG. 5B). The activation of pro-apoptotic members of the Bcl-2 family is linked to mitochondrial dysfunction. It was found that the level of phosphorylated Bad (inactive form), a pro-apoptotic Bcl-2 member, was significantly reduced by maternal diabetes but was restored by trehalose treatment (FIG. 5C). Another pro-apoptotic Bcl-2 member, BID, was activated by cleavage under diabetic conditions; whereas its cleavage was prevented by trehalose (FIG. 5D). Cleaved BID translocates to mitochondria and induces mitochondrial damage (23). Thus, trehalose treatment prevents maternal diabetes-induced mitochondrial dysfunction presumably by removing defective mitochondria through autophagy.

Figure 6:
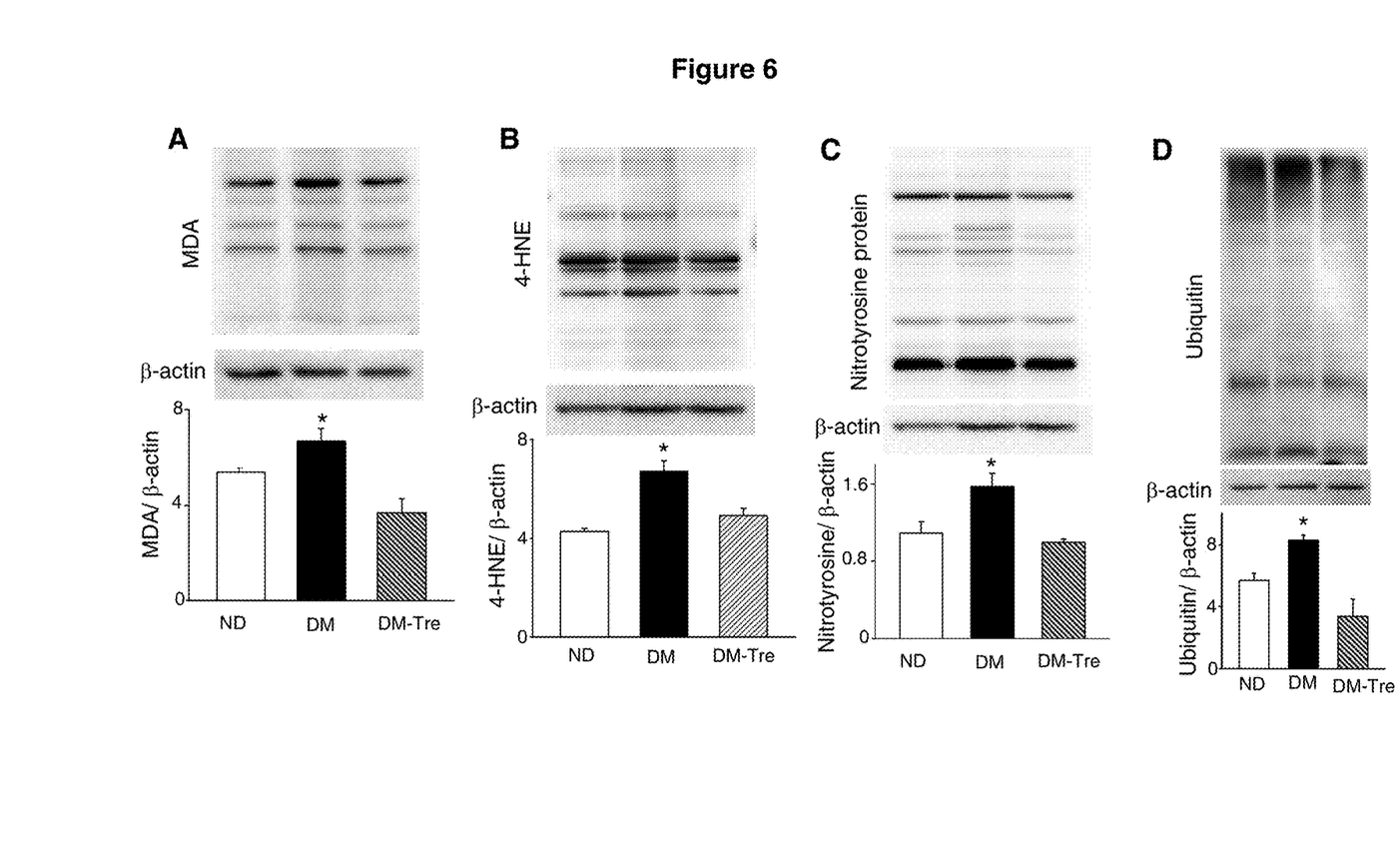

Autophagy removes dysfunctional protein caused by oxidative stress. To determine whether trehalose-induced autophagic activities effectively clear oxidized proteins under diabetic conditions, the levels of two lipidperoxidation markers-4-Hydroxynonenal (4-HNE) and Malondialdehyde (MDA) as well as nitrotyrosine or ubiquitin-modified proteins were assessed. Trehalose blocked maternal diabetes-increased levels of all of these modified proteins (FIGS. 6A, B, C, D).

Caspase 8 and caspase 3 had been previously identified as initiator and effector caspases, respectively, in maternal diabetes-induced apoptosis (21, 22). In this study, it was demonstrated that trehalose treatment abolished maternal diabetes-induced caspase 3 and 8 cleavage (FIG. 5E) and, consequently, blocked neuroepithelial cell apoptosis (FIGS. 5F, G).

Trehalose functionally restores maternal diabetes-impaired neurogenesis during embryonic neurulation. These findings and those of others (11) support the conclusion that autophagy is essential for neural tube closure; however, the functional impact of autophagy on neurogenesis is unclear. Either delayed (24) or advanced (17) neurogenesis causes NTDs. To investigate whether maternal diabetes alters neurogenesis and whether trehalose could correct aberrant neurogenesis, patterns of neural stem cell and neuron marker expression were compared in neural tubes of embryos under nondiabetic and diabetic conditions with or without trehalose treatment.

Figure 7:
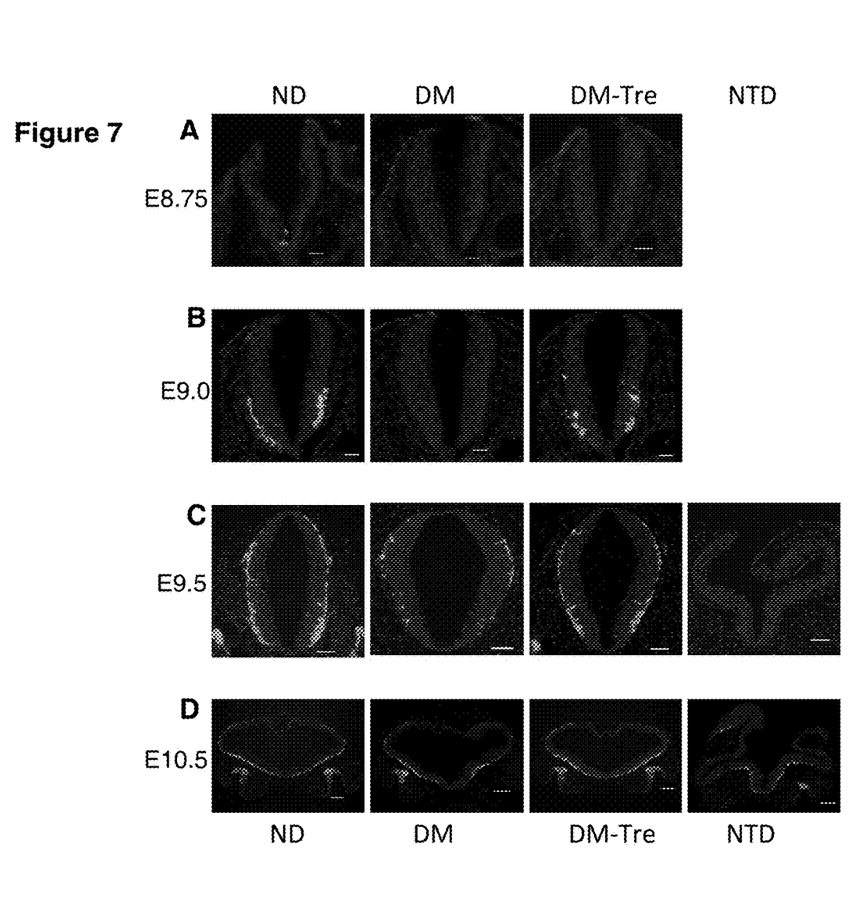

Under nondiabetic conditions, post-mitotic neurons expressing TuJ1 (class III (β-tubulin), a marker of terminal neuronal differentiation, first appeared in the floor plate at E8.75 (FIG. 7A), expanding along the two ventral sides of the developing neural tube at E9.0 (FIG. 7B). They then gradually spread to the entire neural tube from E9.5 to E10.5 (FIGS. 7C, D). Under maternal diabetic conditions, however, TuJ1 expressing neurons were absent in E8.75 and E9.0 neural tubes (FIGS. 7A, B) and appeared in the two ventral sides of closed neural tubes at E 9.5 to much less of a degree than their counterparts in the nondiabetic group (FIG. 7C). At E9.5 TuJ1 expressing neurons were still absent in the open neural tubes of NTD embryos in the diabetic group (FIG. 7C).

At E10.5 the extent of TuJ1 expressing neurons was comparable in closed neural tubes in both the nondiabetic and the diabetic group (FIG. 7D); whereas the open neural tubes in NTD embryos of the diabetic group displayed relative lower amounts of TuJ1-expressing neurons (FIG. 7D). As expected, trehalose reversed delayed neurogenesis due to maternal diabetes (FIGS. 7B, C, D). With trehalose treatment, TuJ1 expressing neurons were observed in E9.0 neural tubes exposed to diabetes with identical expression patterns as those in the nondiabetic group (FIG. 7B). They also expanded in a pattern similar to the pattern observed in the nondiabetic group from E9.5 to E10.5 (FIGS. 7C, D).

Figure 8:
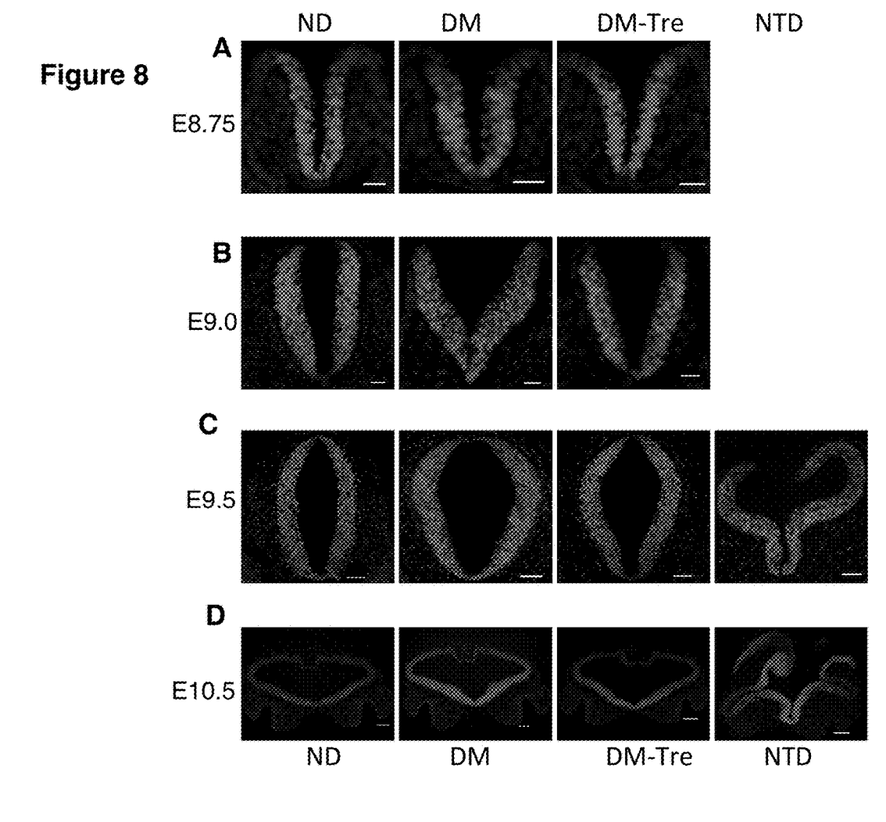

Furthermore, Sox1, a reliable marker of neural precursors, was expressed in most parts of the E8.75 neural tubes (FIG. 8A), but there was reduced expression in the floor plate (where the first neuron appears) in both the nondiabetic and the diabetic with trehalose treatment groups (FIG. 8A). Consistent with the development of neurogenesis, the two ventral sides of the neural tube at E9.0 had gradually diminished Sox1 expression in both the nondiabetic and the diabetic with trehalose treatment groups (FIG. 8B). On the other hand, there was strong Sox1 expression in the entire neural tube of the non-treated diabetic group (FIG. 8B), which had no sign of neurogenesis (FIG. 7B). At E9.5 and E10.5, Sox 1 expression rapidly faded in the closed neural tubes of the three groups; whereas unclosed neural tubes in the diabetic group retained robust Sox1 expression (FIGS.

8C, D). These data suggest that neural precursors are unable to differentiate into neurons under diabetic conditions and, thus, lead to failed neural tube closure and NTD formation.

On the other hand, it was found that trehalose treatment corrected maternal diabetes-blocked differentiation of Sox1 positive neural progenitors and, thus, prevented NTD formation. The critical timing of neural tube closure is between E9.0 and E9.5. Under nondiabetic conditions this is when neurons gradually appeared in the dorsal side where apoptotic cells were mainly present in the diabetic group (FIG. 5F). Thus, these finding also suggests that Sox 1 neural progenitors undergoing neuronal differentiation might undergo apoptosis due to autophagy impairment caused by maternal diabetes.

Discussion

Using multiple approaches, as shown herein it has been determined that autophagy is highly active in neuroepithelial cells of the developing neural tube, and maternal diabetes suppresses this neuroepithelial cell specific autophagic activity. Studies in other disease models have suggested that diabetes may induce autophagy (1, 41). The observation herein that diabetes instead suppresses autophagy is consistent with the finding that activity of the autophagy marker, GAPDH (7), is decreased by hyperglycemia in embryos at neurulation stages (44). Consistent with the fact that NTDs induced by autophagy impairment (11) resemble those observed in diabetic embryopathy, this data supports the hypothesis that impaired autophagy contributes to the pathogenesis of maternal diabetes-induced NTDs.

As shown herein, trehalose re-activates autophagy by restoring LC3-II levels and autophagosome formation in neuroepithelial cells of the developing neural tube and, thus, prevents maternal diabetes-induced NTDs. Trehalose is also shown herein to (a) effectively suppresses ER stress markers and subsequently block neuroepithelial cell apoptosis, which may be attributable to its autophagy stimulatory property; (b) induce removal of damaged mitochondria, important because mitochondrial dysfunction is known to be a key mechanism underlying diabetic embryopathy (49); (c) induce removal of dysfunctional proteins such as lipid-peroxidation markers (4-HNE and MDA), nitrotyrosine, and ubiquitin-modified proteins, important because oxidized proteins are constant features of diabetic embryopathy (43), trehalose thus restores cellular homeostasis by cleaning dysfunctional cellular components and consequently prevents cells undergo apoptosis and NTD formation; and (d) act as an autophagy inducer by facilitating neural progenitor differentiation and correcting delayed neurogenesis.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Adastra K L, Chi M M, Riley J K, and Moley K H. A differential autophagic response to hyperglycemia in the developing murine embryo. Reproduction (Cambridge, England) 141: 607-615, 2011.
2. Barbera J P, Rodriguez T A, Greene N D, Weninger W J, Simeone A, Copp A J, Beddington R S, and Dunwoodie S. Folic acid prevents exencephaly in Cited2 deficient mice. Human molecular genetics 11: 283-293, 2002.
3. Becerra J E, Khoury M J, Cordero J F, and Erickson J D. Diabetes mellitus during pregnancy and the risks for specific birth defects: a population-based case-control study. Pediatrics 85: 1-9, 1990.
5. Chen Q, and Haddad G G. Role of trehalose phosphate synthase and trehalose during hypoxia: from flies to mammals. The Journal of experimental biology 207: 3125-3129, 2004.
6. Chen Y, Azad M B, and Gibson S B. Superoxide is the major reactive oxygen species regulating autophagy. Cell death and differentiation 16: 1040-1052, 2009.
7. Colell A, Ricci J E, Tait S, Milasta S, Maurer U, Bouchier-Hayes L, Fitzgerald P, Guio-Carrion A, Waterhouse N J, Li C W, Mari B, Barbry P, Newmeyer D D, Beere H M, and Green D R. GAPDH and autophagy preserve survival after apoptotic cytochrome c release in the absence of caspase activation. Cell 129: 983-997, 2007.
8. Copp A J, Greene N D, and Murdoch J N. The genetic basis of mammalian neurulation. Nat Rev Genet 4: 784-793, 2003.
9. Correa A, Gilboa S M, Besser L M, Botto L D, Moore C A, Hobbs C A, Cleves M A, Riehle-Colarusso T J, Waller D K, and Reece E A. Diabetes mellitus and birth defects. American journal of obstetrics and gynecology 199: 237 e231-239, 2008.
11. Fimia G M, Stoykova A, Romagnoli A, Giunta L, Di Bartolomeo S, Nardacci R, Corazzari M, Fuoco C, Ucar A, Schwartz P, Gruss P, Piacentini M, Chowdhury K, and Cecconi F. Ambra1 regulates autophagy and development of the nervous system. Nature 447: 1121-1125, 2007.
12. Fujita N, Itoh T, Omori H, Fukuda M, Noda T, and Yoshimori T. The Atg16L complex specifies the site of LC3 lipidation for membrane biogenesis in autophagy. Molecular biology of the cell 19: 2092-2100, 2008.
13. Gareskog M, Cederberg J, Eriksson U J, and Wentzel P. Maternal diabetes in vivo and high glucose concentration in vitro increases apoptosis in rat embryos. Reproductive toxicology (Elmsford, N.Y. 23: 63-74, 2007.
14. Greene M F, Hare J W, Cloherty J P, Benacerraf B R, and Soeldner J S. First-trimester hemoglobin A1 and risk for major malformation and spontaneous abortion in diabetic pregnancy. Teratology 39: 225-231, 1989.
15. Greene N D, and Copp A J. Inositol prevents folate-resistant neural tube defects in the mouse. Nature medicine 3: 60-66, 1997.
16. Inami Y, Waguri S, Sakamoto A, Kouno T, Nakada K, Hino O, Watanabe S, Ando J, Iwadate M, Yamamoto M, Lee M S, Tanaka K, and Komatsu M. Persistent activation of Nrf2 through p62 in hepatocellular carcinoma cells. The Journal of cell biology 193: 275-284, 2011.
17. Ishibashi M, Ang S L, Shiota K, Nakanishi S, Kageyama R, and Guillemot F. Targeted disruption of mammalian hairy and Enhancer of split homolog-1 (HES-1) leads to up-regulation of neural helix-loop-helix factors, premature neurogenesis, and severe neural tube defects. Genes & development 9: 3136-3148, 1995.
19. Levine B, and Yuan J. Autophagy in cell death: an innocent convict? The Journal of clinical investigation 115: 2679-2688, 2005.
20. Li R, Chase M, Jung S K, Smith P J, and Loeken M R. Hypoxic stress in diabetic pregnancy contributes to impaired embryo gene expression and defective develop- 21. Li X, Weng H, Xu C, Reece E A, and Yang P. Oxidative Stress-Induced JNK1/2 Activation Triggers Proapoptotic Signaling and Apoptosis That Leads to Diabetic Embryopathy. Diabetes 61: 2084-2092, 2012.
22. Li X, Xu C, and Yang P. c-Jun NH2-Terminal Kinase 1/2 and Endoplasmic Reticulum Stress as Interdependent and Reciprocal Causation in Diabetic Embryopathy. Diabetes 62: 599-608, 2013.
23. Luo X, Budihardjo I, Zou H, Slaughter C, and Wang X. Bid, a Bcl2 interacting protein, mediates cytochrome c release from mitochondria in response to activation of cell surface death receptors. Cell 94: 481-490, 1998.
24. Lupu F, Alves A, Anderson K, Doye V, and Lacy E. Nuclear pore composition regulates neural stem/progenitor cell differentiation in the mouse embryo. Developmental cell 14: 831-842, 2008.
25. Ly A, Lee H, Chen J, Sie K K, Renlund R, Medline A, Sohn K J, Croxford R, Thompson L U, and Kim Y I. Effect of maternal and postweaning folic acid supplementation on mammary tumor risk in the offspring. Cancer research 71: 988-997, 2011.
26. Miller E, Hare J W, Cloherty J P, Dunn P J, Gleason R E, Soeldner J S, and Kitzmiller J L. Elevated maternal hemoglobin A1c in early pregnancy and major congenital anomalies in infants of diabetic mothers. The New England journal of medicine 304: 1331-1334, 1981.
27. Mizushima N, and Levine B. Autophagy in mammalian development and differentiation. Nature cell biology 12: 823-830, 2010.
28. Mizushima N, Yamamoto A, Matsui M, Yoshimori T, and Ohsumi Y. In vivo analysis of autophagy in response to nutrient starvation using transgenic mice expressing a fluorescent autophagosome marker. Molecular biology of the cell 15: 1101-1111, 2004.
30. Pavlinkova G, Salbaum J M, and Kappen C. Maternal diabetes alters transcriptional programs in the developing embryo. BMC genomics 10: 274, 2009.
32. Ramos-Arroyo M A, Rodriguez-Pinilla E, and Cordero J F. Maternal diabetes: the risk for specific birth defects. European journal of epidemiology 8: 503-508, 1992.
33. Salbaum J M, and Kappen C. Neural tube defect genes and maternal diabetes during pregnancy. Birth Defects Res A Clin Mol Teratol 88: 601-611, 2010.
34. Sarkar S, Davies J E, Huang Z, Tunnacliffe A, and Rubinsztein D C. Trehalose, a novel mTOR-independent autophagy enhancer, accelerates the clearance of mutant huntingtin and alpha-synuclein. The Journal of biological chemistry 282: 5641-5652, 2007.
35. Schaible T D, Harris R A, Dowd S E, Smith C W, and Kellermayer R. Maternal methyl-donor supplementation induces prolonged murine offspring colitis susceptibility in association with mucosal epigenetic and microbiomic changes. Human molecular genetics 20: 1687-1696, 2011.
37. Tanaka M, Machida Y, Niu S, Ikeda T, Jana N R, Doi H, Kurosawa M, Nekooki M, and Nukina N. Trehalose alleviates polyglutamine-mediated pathology in a mouse model of Huntington disease. Nat Med 10: 148-154, 2004.
38. Ting S B, Wilanowski T, Auden A, Hall M, Voss A K, Thomas T, Parekh V, Cunningham J M, and Jane S M. Inositol- and folate-resistant neural tube defects in mice lacking the epithelial-specific factor Grhl-3. Nature medicine 9: 1513-1519, 2003.
39. Tsukamoto S, Kuma A, Murakami M, Kishi C, Yamamoto A, and Mizushima N. Autophagy is essential for preimplantation development of mouse embryos. Science (New York, N.Y. 321: 117-120, 2008.
40. Urano F, Wang X, Bertolotti A, Zhang Y, Chung P, Harding H P, and Ron D. Coupling of stress in the ER to activation of JNK protein kinases by transmembrane protein kinase IRE1. Science (New York, N.Y. 287: 664-666, 2000.
41. Wang A, and Hascall V C. Hyperglycemia, intracellular hyaluronan synthesis, cyclin D3 and autophagy. Autophagy 5: 864-865, 2009.
42. Ward N, Sneddon J, Densem J, Frost C, Stone R, and Group MVSR. Prevention of neural tube defects: results of the Medical Research Council Vitamin Study. MRC Vitamin Study Research Group. Lancet 338: 131-137, 1991.
43. Weng H, Li X, Reece E A, and Yang P. SOD1 suppresses maternal hyperglycemia-increased iNOS expression and consequent nitrosative stress in diabetic embryopathy. American journal of obstetrics and gynecology 206: 448 e441-447, 2012.
44. Wentzel P, Ejdesjo A, and Eriksson U J. Maternal diabetes in vivo and high glucose in vitro diminish GAPDH activity in rat embryos. Diabetes 52: 1222-1228, 2003.
45. Wentzel P, Gareskog M, and Eriksson U J. Folic acid supplementation diminishes diabetes- and glucose-induced dysmorphogenesis in rat embryos in vivo and in vitro. Diabetes 54: 546-553, 2005.
46. Wilson M P, Hugge C, Bielinska M, Nicholas P, Majerus P W, and Wilson D B. Neural tube defects in mice with reduced levels of inositol 1,3,4-trisphosphate 5/6-kinase. Proceedings of the National Academy of Sciences of the United States of America 106: 9831-9835, 2009.
48. Yang P, Zhao Z, and Reece E A. Involvement of c-Jun N-terminal kinases activation in diabetic embryopathy. Biochemical and biophysical research communications 357: 749-754, 2007.
49. Yang X, Borg L A, and Eriksson U J. Altered mitochondrial morphology of rat embryos in diabetic pregnancy. The Anatomical record 241: 255-267, 1995.

What is claimed is:

1. A method for reducing the risk of a hyperglycemia-induced neural tube defect in an embryo, comprising administering a therapeutically-effective amount of a pharmaceutical formulation consisting of trehalose-in-water to a pregnant subject or a subject intending to become pregnant, wherein the subject is hyperglycemic, wherein the therapeutically-effective amount of the formulation is an amount that achieves between about 260 and 500 ug/ml trehalose in the maternal blood, wherein when the subject is pregnant, the therapeutically-effective amount of the formulation is administered daily through the first month of pregnancy, and wherein when the subject is intending to become pregnant, the therapeutically-effective amount of the formulation is administered daily from a few days before the date on which conception is attempted through the first month of pregnancy.

2. The method of claim 1, wherein the hyperglycemia is diabetes mellitus-induced hyperglycemia, drug-induced hyperglycemia, or illness-induced hyperglycemia.

3. The method of claim 1, wherein the neural tube defect is failure of neural tube closure.

4. The method of claim 1, wherein the therapeutically-effective amount of the formulation is an amount that achieves about 350 ug/ml trehalose in the maternal blood.

5. The method of claim 1, wherein the therapeutically-effective amount of the formulation is administered to the subject orally or via parenteral administration.

6. A method for preventing a hyperglycemia-induced neural tube defect in an embryo, comprising administering a therapeutically-effective amount of a pharmaceutical formulation consisting of trehalose-in-water to a pregnant subject or a subject intending to become pregnant, wherein the subject is hyperglycemic, wherein the therapeutically-effective amount of the formulation is an amount that achieves between about 260 and 500 ug/ml trehalose in the maternal blood, wherein when the subject is pregnant, the therapeutically-effective amount of the formulation is administered daily through the first month of pregnancy, and wherein when the subject is intending to become pregnant, the therapeutically-effective amount of the formulation is administered daily from a few days before the date on which conception is attempted through the first month of pregnancy.

7. The method of claim 6, wherein the hyperglycemia is diabetes mellitus-induced hyperglycemia, drug-induced hyperglycemia, or illness-induced hyperglycemia.

8. The method of claim 6, wherein the neural tube defect is failure of neural tube closure.

9. The method of claim 6, wherein the therapeutically-effective amount of the formulation is an amount that achieves about 350 ug/ml trehalose in the maternal blood.

10. The method of claim 6, wherein the therapeutically-effective amount of the formulation is administered to the subject orally or via parenteral administration.

* * * * *